United States Patent [19]

Siri

[11] Plant 5,216

[45] Apr. 10, 1984

[54] MINIATURE CARNATION

[75] Inventor: Angelo J. Siri, San Francisco, Calif.

[73] Assignee: Siri Brothers Nursery, Inc., East Palo Alto, Calif.

[21] Appl. No.: 397,113

[22] Filed: Jul. 12, 1982

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Limbach, Limbach & Sutton

[57] ABSTRACT

A miniature carnation having blossoms with white petals having pale lilac stripes and blotches.

1 Drawing Figure

BACKGROUND OF THE NEW PLANT

This invention comprises a new and distinct miniature carnation variety that has its own set of characteristics that set it apart from all other varieties of miniature carnations. The newly discovered variety, called "Parfait," originated as a sport of Lilac, an unpatented variety.

The botanical classification of the new variety is *Dianthus caryophyllus longicaulis.* The commercial classification is Miniature Carnation. The plant takes the form of a bush.

Asexual propagation of the newly discovered miniature carnation variety has been made at Siri Brothers Nursery, Inc. at East Palo Alto, Calif. by taking cuttings. The cuttings so taken and grown, have consistently produced flowers that have the new and distinct characteristics hereinafter described.

DESCRIPTION OF THE DRAWINGS

This new variety of miniature carnation plant is illustrated by the accompanying drawings which show the color characteristics of the flower as nearly true as it is reasonably possible to obtain through conventional photographic procedures.

DESCRIPTION OF THE NEW PLANT

Figure 1:
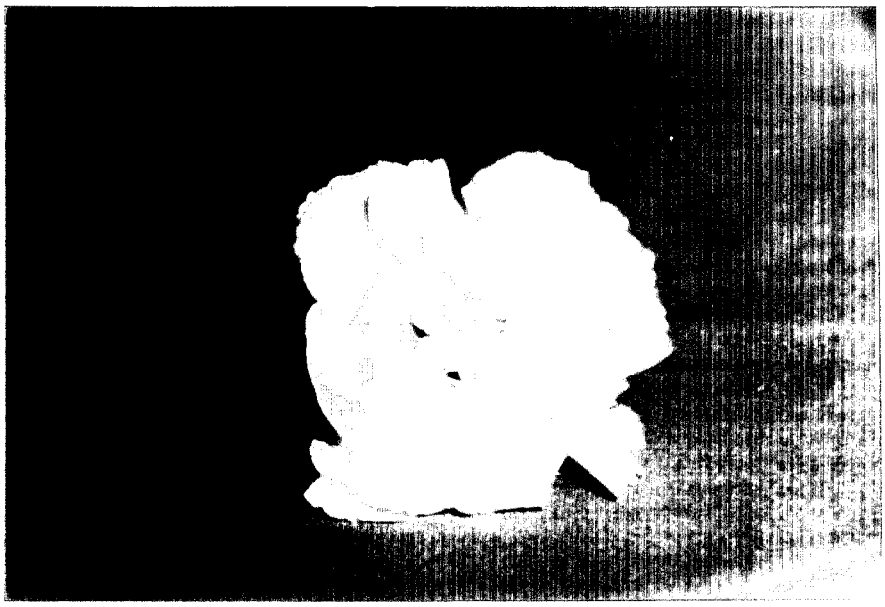
FIG. 1 shows the bloom of the new variety Parfait.

The following detailed description of the new variety is based on my detailed observations of the new cultivar which were made at Siri Brothers Nursery Inc. at 940 O'Connor St., East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore Md. and "R.H.S." for Royal Horticultural Colour Chart, The Royal Horticultural Society, London, England.

GROWTH HABITS

Height: Short to medium.
Foliage: Average.
Speed of growth: Fast.
Root system: Average.

FOLIAGE

Leaf size:
- *Length.*—Varies: Longer at the bottom of the stem and shorter at the top. Average at the middle of the stem is 4¼ inches.
- *Width.*—Varies: Wider at the bottom of the stem and thinner at the top. Average at the middle of the stem is 7/16 of an inch.
- *Features.*—N/A.

Leaf shape: Very little curl with a long acuminating tip.
Leaf texture: Smooth and leathery.
Leaf color:
- *Upperside.*—R.H.S. Green Group 136A with a whitish color over the green.
- *Underside.*—R.H.S. Green Group 136A with a whitish color over the green.

Leaf ribs: One rib down the center from the base to the tip of the leaf.
Leaf habit: Very little curl.
Leaf density: Average.

STEM

Stem strength: Average.
Stem color: R.H.S. 136A Green Group with a whitish color over the green.
Nodes: Average.
- *Space between nodes.*—3½ inches average at mid-stem.

Stem branching: Very good, wide gaps between the branches, not clubby.

BUDS

Bud shape: Oval.
Bud color: The top half of the bud is LCC H-21 L-13. The bottom half blends into LCC H-22 L-9.
Average number of flowering buds per stem: 4–5.
Uniformity of bud opening: Very uniform.
Bud splitting: Very seldom.
Number of sepals per calyx: 60% have 5; 30% have 6; 10% have 7.

FLOWER

Description of the color of the bloom: This bloom is white (R.H.S. White Group 155D) with Lilac colored blotches (LCC H-44 L-2 underside of petal and LCC H-44 L-3 topside of petal) and stripes of varying size running from the base of the bloom to the outer edge. However there are some Lilac stripes and blotches that run in the petal but do not touch the base or the outer edge. The lilac color and the white color are random on the petal. There are even some petals that are completely white or completely lilac. There is no exact set pattern although there is a consistent one. Occasionally, a very small fleck of dark purple LCC H-43 L-14 appears on a petal.

General tonality of the color: Soft. Two soft delicate pastel shades.
Diameter of average bloom: 2 inches.
Bloom shape: Generally round with a high center and a flat outer petal.
Keeping quality: Average.
Fragrance: Slight.

PETALAGE

Petal texture: Soft and velvety.
Petal edge: Medium to slight serration.
Petal color: As stated above.
Color stability: Excellent. There is only a slight reversion to Lilac.
Petal Size:
Average length.—1½ inches.
*Average width at widest point.*—9/16 of an inch.
Calyx color: Top half LCC H-21 L-13, the bottom half blends into LCC H-22 L-9. The tips of the leaves on the bottom of the calyx are LCC H-22 L-15.

REPRODUCTIVE ORGANS

Stamen: Approximately 90% have anthers and 10% don't.
Average length of stamen: 1 inch.
Color of anthers: LCC H-44 L-1.
Color of filament: LCC H-22 L-1.
Pistils:
*Shape.*—Approximately 85% have 2 styles and 15% have 3 styles.

*Number.*—One.
*Length from tip to ovary.*—⅞ of an inch.
Stigma:
*Shape.*—Round.
*Color.*—White, it is located at the very tip of the style.
Style:
*Color.*—Bottom LCC H-25 L-1, toward tip LCC H-43 L-13.
Ovary:
*Shape.*—Ovid.
*Color.*—The tip is LCC H-26 L-10, the top half is LCC H-23 L-9, the bottom half is LCC H-23 L-1.
*Length.*—Approximately ⅜ of an inch.
*Width.*—Approximately 3/16 of an inch.

DISTINGUISHING CHARACTERISTICS BETWEEN THE NEW VARIETY AND PARENT

The primary distinguishing characteristic of the two varieties is the color. Lilac is a solid Lilac color and Parfait is a varigation of White and Lilac. The color of the anthers in a Lilac bloom is LCC H-48 L-2 while the color of the anthers in a Parfait bloom are LCC H-44 L-1. The color of the tip of the styles in both Lilac and Parfait are the same (LCC H-43 L-13). However, there is much more of a concentration of that color on the styles of Lilac than on the styles of Parfait.

SIMILAR CHARACTERISTICS OF THE NEW VARIETY AND PARENT

All of the characteristics of both varieties are similar except for the distinguishing characteristics referred to above.

I claim:

1. A new and distinct variety of miniature carnation plant, substantially as herein shown and described.

* * * * *